United States Patent [19]

Doherty

[11] 4,160,450
[45] Jul. 10, 1979

[54] OUTSIDE-THE-NEEDLE CATHETER DEVICE WITH NEEDLE HOUSING

[76] Inventor: George O. Doherty, 2301 River Rd., Missoula, Mont. 59801

[21] Appl. No.: 815,806

[22] Filed: Jul. 15, 1977

[51] Int. Cl.$^2$ .............................................. A61M 5/00
[52] U.S. Cl. ........................ 128/214.4; 128/DIG. 16
[58] Field of Search ................... 128/214.4, 221, 347, 128/348, DIG. 16

[56] References Cited

U.S. PATENT DOCUMENTS

| 2,389,355 | 11/1945 | Goland et al. | 128/214.4 |
| 3,262,449 | 7/1966 | Pannier et al. | 128/214.4 |
| 3,547,119 | 12/1970 | Hall et al. | 128/214.4 |

FOREIGN PATENT DOCUMENTS 378629  7/1923  Fed. Rep. of Germany ........ 128/214.4

Primary Examiner—Dalton L. Truluck
Attorney, Agent, or Firm—Mallinckrodt & Mallinckrodt

[57] ABSTRACT

A catheter device, comprising a venipuncture needle or stylet whose shank extends through the bore of a catheter or cannula and has a sharpened tip projecting slightly therebeyond in an extended position of the needle to provide an outside-the-needle catheter unit for venipuncture and for insertion of the catheter in a vein in largely conventional manner, and a housing adapted to define an elongate liquid flow chamber. Such housing is connected, liquid-tight, at one end to the catheter and is adapted to protectively house the sharpened tip of the needle following venipuncture. The housing itself is liquid-tight, except for an opening at its other end through which extends tubing for the supply of a venoclysis liquid. The other end of the needle may be provided with a hub formed as a stopper for fitting tightly in a seat formed in the housing immediately in advance of the opening, or may be provided with a hub that is attached to the supply tubing at the opening. In the latter instance, the housing is collapsible and attached, liquid-tight, to the supply tubing so the catheter can be advanced into the vein relative to the needle. In the former instance, the needle is retractable relative to the catheter and housing. In all instances, the length of the portion of the needle disposed within the catheter and extending beyond the free end thereof is less than the length of the liquid flow chamber, so liquid supplied through the hollow interior of the needle will flow into such chamber and then into and through the catheter.

10 Claims, 7 Drawing Figures

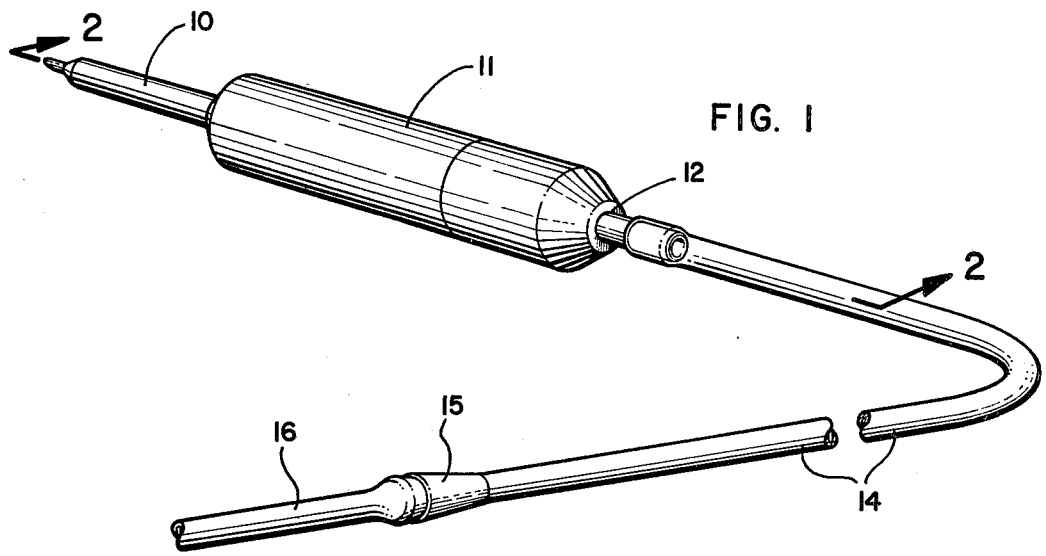
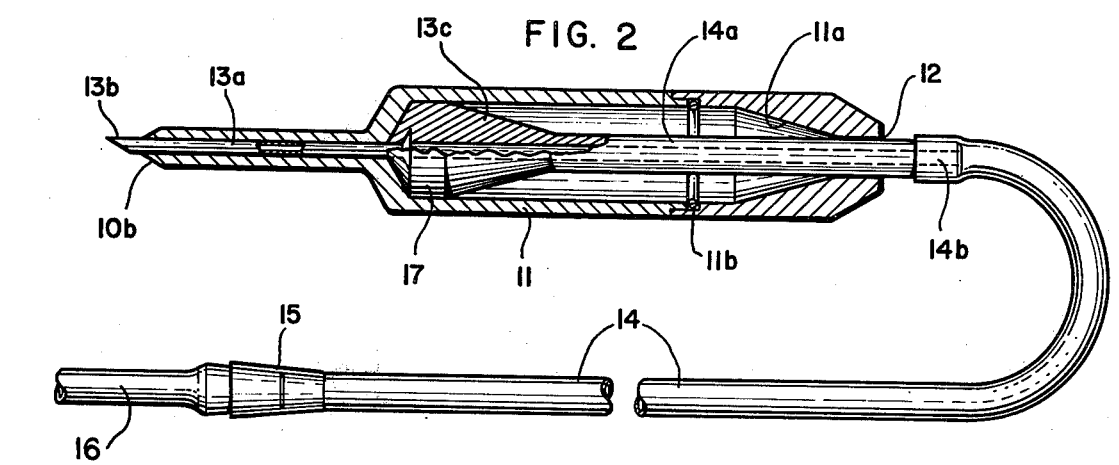
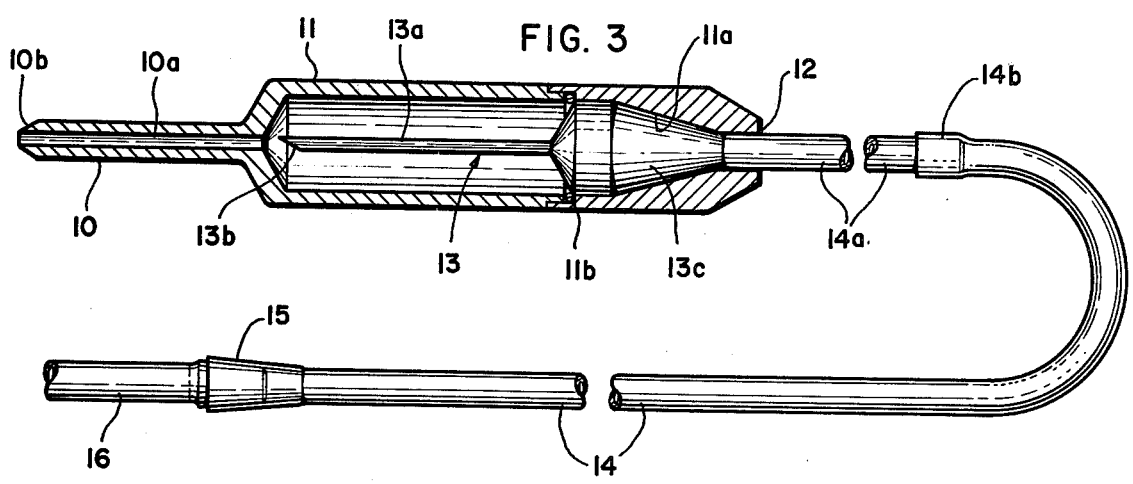

OUTSIDE-THE-NEEDLE CATHETER DEVICE WITH NEEDLE HOUSING

BACKGROUND OF THE INVENTION

1. Field

The invention is in the field of catheter devices of outside-the-needle type, as employed for supplying liquids intravenously.

2. State of the Art

Devices of the type concerned are well known and widely used for intravenous administration of various liquids, such as parenteral solutions, for blood transfusions, etc. Such devices may also be adapted in known manner to remove liquids from the body for a variety of purposes, such as for the making of medical laboratory tests.

As originally constructed, outside-the-needle catheter devices have suffered from messy blood spillage and contamination during the time the venipuncture needle has been withdrawn from the catheter or cannula immediately after placement of the catheter in a vein and before the venoclysis set has been connected to the catheter. This has been highly undesirable for a variety of reasons. Besides being unsanitary and inconvenient, it has tended to frighten the patient.

Subsequent designs utilizing a Y-formed (side-arm-provided) hub for the catheter, so the venoclysis set can be connected to one branch of the Y formation prior to venipuncture and subsequent withdrawal of the needle, have not eliminated the problems even though they have helped considerably. Following venipuncture, withdrawal of the needle from the puncture-hole through the rubber sealing cap that is provided on the other branch of the Y formation has resulted in messy and undesirable leakage of venoclysis liquid, usually mixed with the initial backflow blood, during administration of such liquid. The desired and expected automatic sealing of the cap following needle withdrawal does not normally work out in practice due to a tendency for the defining margins of the puncture-hole through the rubber or flexible plastic materials to acquire a "set" over usual shelf-life time periods, thus allowing leakage.

SUMMARY OF THE INVENTION

In accordance with the invention, the above-mentioned problems are effectively solved by providing an elongate needle-receiving housing having one end connected in liquid-tight manner to a catheter through which extends a stylet needle having an end enclosed by the housing. The housing is itself liquid-tight, except for an opening in its end opposite the catheter. A tube, usually supply tubing for a venoclysis liquid, extends through and substantially closes such opening and connects with the enclosed end of the needle. The needle is entirely free of the catheter, but remains within the housing, following withdrawal from the vein. Flow of liquid takes place via the interior of the housing.

Means are provided by which the housing opening is closed liquid-tight. In one embodiment of the device, such means takes the form of a seat in the housing and a hub formation on the enclosed end of the needle for liquid-tight engagement with the seat when the needle is retracted into the housing. In other embodiments wherein the catheter is advanced relative to the needle, such means takes the form of a liquid-tight connection between the housing and the tube that enters the housing through the opening.

The housing and at least the supply tubing for the venoclysis liquid are preferably of transparent or translucent material, usually a suitable synthetic resin plastic, whereby flash-back of blood can be observed to indicate a successful venipuncture. It is a feature of the invention that the needle is wholly withdrawn from the catheter following venipuncture, so danger of inadvertent transection of the catheter by the sharp end of the needle is minimized.

THE DRAWING

Embodiments representing the best mode presently contemplated for utilizing the invention in actual practice are illustrated in the accompanying drawing, in which:

FIG. 1 is a pictorial view of one embodiment showing the device connected to the supply tubing of a venoclysis set and ready for venipuncture;

FIG. 2, a vertical axial section taken along the line 2—2 of FIG. 1 and showing the venoclysis tubing in elevation;

FIG. 3, a view corresponding to that of FIG. 2 but showing the stylet needle retracted into stoppering position as it would be following venipuncture;

FIGS. 4 and 5, views corresponding to those of FIGS. 2 and 3, respectively, but showing a different embodiment of the invention; and FIGS. 6 and 7, views corresponding to FIGS. 4 and 5, respectively, but showing a variation of the embodiment of FIGS. 4 and 5.

DETAILED DESCRIPTION OF THE ILLUSTRATED EMBODIMENTS

Figure 4:
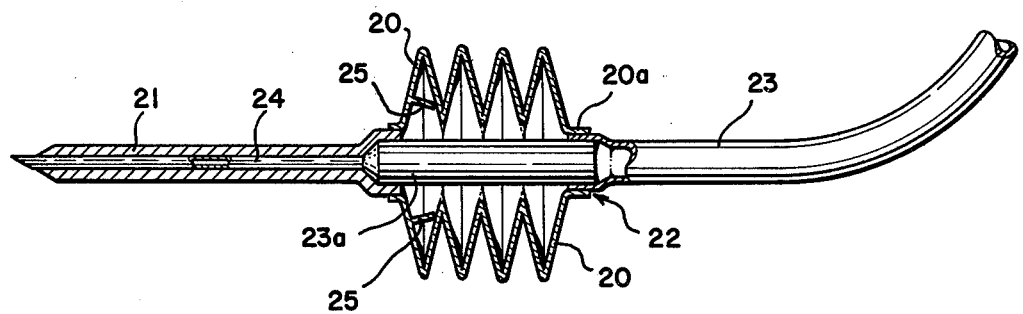

In the embodiment of FIGS. 1–3, the catheter device of the invention comprises a catheter or cannula 10 of any suitable length connected integrally or otherwise in a liquid-tight manner to an elongate housing 11, which is itself liquid-tight except for an opening 12 opposite the bore 10a of the catheter.

Fitted into catheter 10 in the ready-to-use condition of the catheter device as illustrated in FIGS. 1 and 2, is the shank 13a of a hollow stylet needle 13. The usual sharp venipuncture point 13b of needle 13 protrudes somewhat beyond the annularly beveled insertion tip 10b of catheter 10, as is usual in an outside-the-needle catheter device, to facilitate venipuncture. A hub 13c of stopper formation is provided within housing 11 at the blunt end of needle shank 13a opposite the sharp end. As shown, hub 13c is of a plastic material molded about the blunt end of needle shank 13a so as to be rigidly secured thereto. Such needle shank is usually of steel.

Internally of housing 11, the walls 11a immediately in advance of opening 12 are formed to receive and seat needle hub 13c in a sealing, stoppering fit, as illustrated in FIG. 3, when needle 13 is retracted. As a safeguard against possible transection of catheter 10 by inadvertent movement of needle 13 from its stoppering position of FIG. 3, a detent "snap" ring 11b or equivalent is preferably provided internally of housing 11 at the forward margin of seat 11a for stopper hub 13c of needle 13.

Venoclysis connection tubing 14 extends (from a fluid-tight, removable connection 15 with the usual discharge tubing 16 of a conventional venoclysis set, when in use) through opening 12 of housing 11 to a secure connection with hub 13c of needle 13. As shown, needle hub 13c is formed integrally with a rigid or semi-rigid portion 14a of connection tubing 14 and is preferably of a transparent or translucent plastic material molded about the proximal end of needle shank 13a, which is usually of steel. The remainder of connection tubing 14 is preferably flexible, as is customary, and connects with portion 14a in a tight, overlapping fit 14b. Housing 11 may be formed in two tightly interfitting and sealed sections, with interposed detent ring, as illustrated, to facilitate assembly.

It should be realized that the particular materials and connections employed are subject to wide variation in accordance with acceptable fabrication, sterilization, and packaging technology for mass production of the catheter devices of the invention, all according to knowledge readily available to the art. Also, as is now customary in the art, all components are advantageously sterile for immediate use, disposable after use, and packaged to maintain sterility up until time of use.

The material used for housing 11, ordinarily a suitable plastic material such as polyethylene, etc., may be rigid or semi-rigid if, as previously indicated, portion 14a of connection tubing 14 is rigid or semi-rigid, and can be held at its exterior end just forwardly of and at connection 14b to prevent backward movement of the needle during venipuncture and to withdraw the needle after venipuncture. Otherwise, such material should be sufficiently flexible to enable manual pressure exerted against the exterior of the housing at its forward end and about needle hub 13c in the position shown in FIG. 2 to prevent backward movement of the needle during venipuncture. The connections between needle shank 13a, needle hub 13c, and venoclysis connection tubing 14 should be sufficiently secure to insure against separation when such tubing 14 is pulled backwardly to withdraw the needle for catheter or cannula 10 and to seat hub 13c firmly against and in sealing relationship with the housing walls 11a immediately in advance of opening 12.

Although needle hub 13c and housing 11 are shown as being slidably interfaced at 17 for guidance purposes and to enhance sealing, this is an optional feature. There need be no interfacing except where seating effects plugging and sealing of opening 12.

The device of the invention is used in much the same way as are conventional outside-the-needle catheter devices. A vein of the patient concerned is punctured in conventional manner by forcing the protruding point 13b of needle 13 and the beveled tip 10b of catheter 10 through overlying skin and flesh of the patient and into the vein, the backwardly protruding end 14b of rigid or semi-rigid connection tubing 14a being held firmly along with housing 11 during this time. Flash-back of blood, observable through transparent or semi-transparent needle hub 13c, portion 14a of connection tubing 14, and housing 11, indicates a successful venipuncture.

While still firmly holding end 14b of connection tubing 14 with one hand, housing 11 is pushed forwardly by the other hand to advance catheter 10 relative to needle shank 13a farther into the vein. Then housing 11 is held stationary while portion 14a is pulled backwardly until needle hub 13c is securely seated as a stopper against walls 11a behind detent ring 11b, as shown in FIG. 3. In preferred embodiments, needle shank 13a and pointed end 13b will be entirely withdrawn from catheter 10 and protectively encased by housing 11.

With the needle retracted in this manner, housing 11 is pushed forwardly to advance catheter 10 as far as desired into the vein. The device is then anchored in place in customary manner by the use of adhesive tape.

Figure 5:
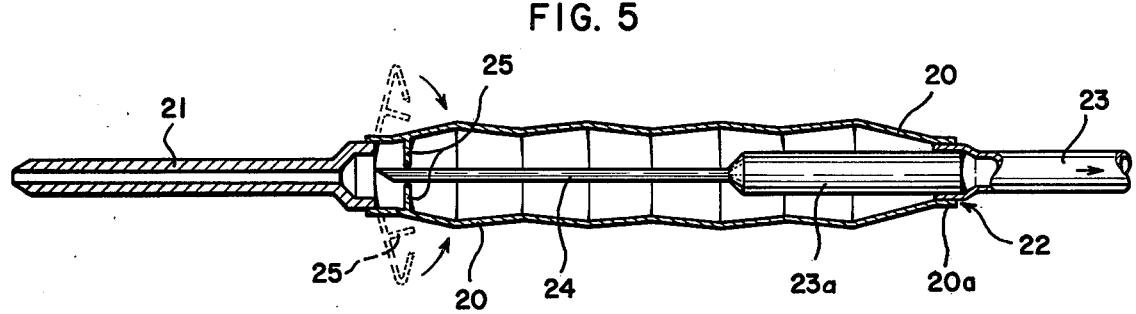
Figure 6:
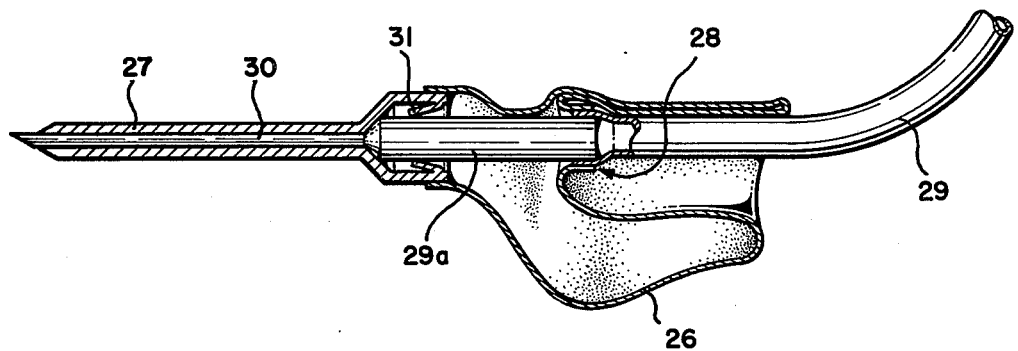
Figure 7:
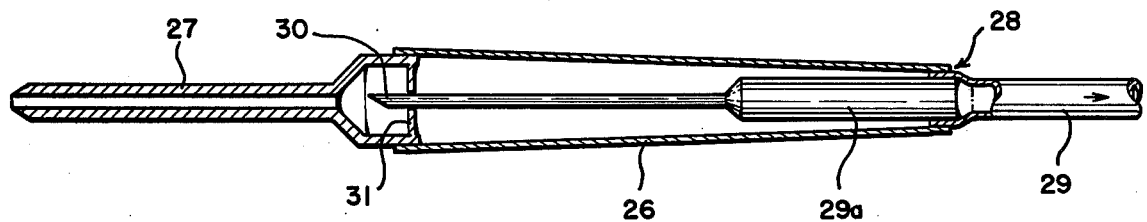

The embodiments of FIGS. 4 and 5 and of FIGS. 6 and 7 differ from the embodiment of FIGS. 1-3 in both construction and use, but are similar in that each provides a housing for the stylet needle following venipuncture, which housing is liquid-tight and serves to channel liquid between the needle, as withdrawn from the vein of a patient after venipuncture, and the catheter that remains in the vein after needle withdrawal. In both of these embodiments, the housing is secured liquid-tight to the entering tube at the opening through which such tube enters, and the housing is constructed so the catheter can be advanced relative to the needle, rather than the needle retracted relative to the catheter.

In the embodiment of FIGS. 4 and 5, the housing is shown at 20 as of bellows formation, with a catheter 21 extending from liquid-tight securement thereto (as by being molded integrally therewith from a suitable plastic) at one end and with an opening 22 axially of the other end through which extends a tube 23, usually for the supply of a venoclysis liquid as previously described. In order to make housing 20 liquid-tight, its end 20a is sealed to tube 23 in some suitable manner as by heat-sealing or by applying an adhesive.

Hollow stylet needle 24 has an elongate hub, which forms a potion 23a of tube 23 and is secured to the main portion of such tube in any convenient manner, as by applied adhesive at opening 22.

Prior to venipuncture, housing bellows 20 is contracted as in FIG. 4, with needle 24 extending through and projecting somewhat beyond the bore of cathether 21. Venipuncture is effected by pressing cathether 21 tightly against the shank 24 and advancing both together toward and into the vein. Thus, needle hub 23a is held with one hand while catheter 21 is advanced into the vein along and relative to the shank of needle 24, until such needle 24 is entirely within extended bellows housing 20 as in FIG. 5. It is preferred to provide an internally projecting annulus 25 internally of housing 20 for maintaining the shank of needle 24 near axial position within the extended housing.

In the embodiment of FIGS. 6 and 7, the housing 26 is like a bag, having walls that are doubled back reentrantly and hang limp prior to venipuncture, as in FIG. 6. One end is connected liquid-tight to catheter 27, and an opening 28 axially of the other end receives a tube 29 which has a portion 29a connected liquid-tight to needle 30 as a hub therefor. Bag housing 26 is connected liquid-tight to tube 29, so as to be sealed tightly against leakage at all times, and an internally projecting annulus 31 is provided as in the embodiment of FIGS. 4 and 5 for maintaining the shank of needle 30 near axial position within the extended housing.

Venipuncture and advancement of catheter 27 into the vein are effected as with the embodiment of FIGS. 4 and 5, leaving needle 30 within bag housing 26 in the fully extended position of such housing.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A catheter device, comprising a catheter having a free end for insertion in a venipuncture; a housing connected liquid-tight at one of its ends to an end of the catheter for liquid flow therebetween, said housing being adapted to define an elongate, liquid flow chamber internally thereof and being itself liquid-tight except for an opening through its end opposite the catheter; a hollow, stylet needle having a sharp end adapted to extend beyond the free end of the catheter to effect venipuncture, and a shank adapted to extend through the catheter internally thereof and into the said flow chamber of the housing during venipuncture, the length of the portion of the needle disposed within the catheter and extending beyond the free end thereof during venipuncture being less than the maximum length of said liquid flow chamber of the housing, so extended movement of the needle relative to the housing or vice versa following venipuncture will protectively position the sharp end of the needle within said housing and liquid supplied through the hollow interior of the needle will flow into said chamber and thence into and through said catheter; a tube for the supply of a venoclysis liquid extending through and substantially closing said opening and connected liquid-tight to the needle; and means by which said opening is closed liquid-tight.

2. A catheter device in accordance with claim 1, wherein the tube is slidable within the housing opening, the end portion of the housing opposite the catheter is formed as a seat; and the means by which said opening is closed liquid-tight is a hub formation on the end of the needle that is within the housing, said hub formation being shaped to fit liquid-tight against said seat when the needle is retracted into the housing.

3. A catheter device in accordance with claim 2, wherein the portion of the tube which is connected to the needle and which extends through the opening is rigid or semi-rigid to enable manipulation of the needle from outside the housing.

4. A catheter device in accordance with claim 2, wherein the housing seat and the needle hub formation are conical.

5. A catheter device in accordance with claim 2, wherein the walls of the housing are flexible so the needle can be manipulated from outside the housing by manipulative pressure against said walls of the housing.

6. A catheter device in accordance with claim 2, wherein the needle hub has a longitudinal portion interfaced with the housing.

7. A catheter device in accordance with claim 2, wherein there is provided detent means internally of the housing at the forward margin of the seat to retain the needle in its retracted position.

8. A catheter device in accordance with claim 1, wherein the walls of the housing are collapsible and collapsed in the venipuncture position of the device so the catheter can be advanced relative to the needle following venipuncture; and the means by which the housing opening is closed liquid-tight is a liquid-tight connection between the housing and the tube.

9. A catheter device in accordance with claim 8, wherein the collapsible housing walls are formed as bellows.

10. A catheter device in accordance with claim 8, wherein the collapsible housing walls are of limp material hanging loosely in the venipuncture position of the device.

* * * * *